(12) United States Patent
Fan et al.

(10) Patent No.: US 9,789,038 B2
(45) Date of Patent: Oct. 17, 2017

(54) ANTIPERSPIRANT/DEODORANT COMPOSITIONS

(75) Inventors: Aixing Fan, Bridgewater, NJ (US); H. Steven Misner, Verona, NJ (US); Suzanne Jogun, Wayne, NJ (US); Stacy Alfone, Hillsborough, NJ (US); Mary Bertino, Franklin Park, NJ (US); Fernando Cotero, Pinehurst, NC (US); Richard Peter Adams, Monmouth Junction, NJ (US); Elizabeth Linn, Lyndhurst, NJ (US); Hemani Dharia, Chicago, IL (US); Roger Broadwell, Dover, NJ (US); John A. Van Duyne, Jr., Rockaway, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 1646 days.

(21) Appl. No.: 11/972,882

(22) Filed: Jan. 11, 2008

(65) Prior Publication Data
US 2008/0187504 A1 Aug. 7, 2008

Related U.S. Application Data

(63) Continuation-in-part of application No. 11/670,481, filed on Feb. 2, 2007, now abandoned.

(51) Int. Cl.
| | |
|---|---|
| *A61K 8/02* | (2006.01) |
| *A61K 8/34* | (2006.01) |
| *A61K 8/04* | (2006.01) |
| *A61K 8/39* | (2006.01) |
| *A61K 8/58* | (2006.01) |
| *A61K 8/92* | (2006.01) |
| *A61Q 15/00* | (2006.01) |

(52) U.S. Cl.
CPC ............ *A61K 8/342* (2013.01); *A61K 8/0216* (2013.01); *A61K 8/0229* (2013.01); *A61K 8/042* (2013.01); *A61K 8/39* (2013.01); *A61K 8/585* (2013.01); *A61K 8/922* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 4,120,948 A | 10/1978 | Shelton | |
| 4,202,879 A | 5/1980 | Shelton | |
| 5,134,130 A | 7/1992 | Shaw et al. | |
| 5,254,332 A * | 10/1993 | Grezcyn | A61K 8/0229 424/65 |
| 5,487,887 A | 1/1996 | Benfatto | |
| 5,599,555 A * | 2/1997 | El-Nokaly | 424/488 |
| 5,726,163 A * | 3/1998 | Fujii et al. | 514/78 |
| 5,744,130 A | 4/1998 | Guskey et al. | |
| 5,846,520 A | 12/1998 | Guskey et al. | |
| 5,902,572 A | 5/1999 | Luebbe et al. | |
| 5,932,199 A | 8/1999 | Esser | |
| 6,007,799 A | 12/1999 | Lee et al. | |
| 6,048,518 A | 4/2000 | Bianchi et al. | |
| 6,086,887 A | 7/2000 | Parrott | |
| 6,099,827 A | 8/2000 | Esser | |
| 6,171,601 B1 | 1/2001 | Gardlik et al. | |
| 6,177,066 B1 | 1/2001 | Patuat et al. | |
| 6,221,345 B1 | 4/2001 | Esser | |
| 6,231,842 B1 | 5/2001 | Scavone et al. | |
| 6,352,688 B1 | 3/2002 | Scavone et al. | |
| 6,372,234 B1 | 4/2002 | Deckers et al. | |
| 6,372,235 B1 | 4/2002 | Livoreil et al. | |
| 6,375,938 B1 | 4/2002 | Clothier, Jr. et al. | |
| 6,383,476 B1 | 5/2002 | Scavone et al. | |
| 6,485,716 B1 | 11/2002 | Fei et al. | |
| 6,503,491 B2 * | 1/2003 | Guenin et al. | 424/65 |
| 6,511,658 B2 | 1/2003 | Mattai et al. | |
| 6,534,045 B2 | 3/2003 | Mattai et al. | |
| 6,713,051 B2 | 3/2004 | Mayes et al. | |
| 6,797,020 B2 | 9/2004 | Murphy | |
| 6,849,251 B2 | 2/2005 | Banowski et al. | |
| 6,969,510 B2 | 11/2005 | Holerca et al. | |
| 7,105,691 B2 | 9/2006 | Holerca et al. | |
| 2003/0061760 A1 | 4/2003 | Tao et al. | |
| 2003/0206973 A1 | 11/2003 | Gale | |
| 2003/0207971 A1 | 11/2003 | Stuart, Jr. et al. | |
| 2004/0028628 A1 | 2/2004 | Guenin et al. | |
| 2004/0120909 A1 | 6/2004 | Lee et al. | |

(Continued)

FOREIGN PATENT DOCUMENTS

| | | |
|---|---|---|
| EP | 1 005 853 | 7/2002 |
| EP | 1529521 | 5/2005 |

(Continued)

OTHER PUBLICATIONS

U.S. Appl. No. 10/571,488, filed Sep. 9, 2004 to Popoff et al.
"Oil yields and characteristics". Retrieved from www.journeytoforever.org on Jul. 14, 2006.
U.S. Appl. No. 11/670,472, filed Feb. 2, 2007 to Popoff et al.
File History for U.S. Appl. No. 11/670,470.
File History for U.S. Appl. No. 11/670,472, filed Feb. 2, 2007; Popoff et al.
Noro et al., "Evaluation of the emulsifying activity of saturated egg phosphatide hydrogenation for the O/W type emulsion", Yakugaku Zasshi, 105 (7): 634-9, 1985.
21CFR 350.3, Apr. 1, 2006.
Shurset 125, partially hydrogenated soybean oil product specification, Jan. 3, 2001.
File History U.S. Appl. No. 11/670,481.

(Continued)

*Primary Examiner* — Johann R Richter
*Assistant Examiner* — Danielle Sullivan

(57) ABSTRACT

A composition comprising at least one active chosen from at least one antiperspirant active and at least one deodorant active; a first gellant chosen from at least one fatty alcohol and at least one hydrocarbon of the formula $C_nH_{2n+2}$, wherein n is about 20 to about 100, and the hydrocarbon is at least 90% linear; at least one soybean oil having an iodine value of greater than 0 to about 20; and at least one silicone.

18 Claims, 1 Drawing Sheet

(56) References Cited

U.S. PATENT DOCUMENTS

| | | |
|---|---|---|
| 2004/0197281 A1 | 10/2004 | Walling et al. |
| 2004/0234468 A1 | 11/2004 | Kerschner et al. |
| 2005/0048013 A1 | 3/2005 | Diec et al. |
| 2005/0281767 A1 | 12/2005 | Walling et al. |
| 2005/0281851 A1 | 12/2005 | Cap |
| 2005/0287069 A1 | 12/2005 | Walling et al. |
| 2006/0018855 A1 | 1/2006 | Batista et al. |
| 2006/0115441 A1 | 6/2006 | James et al. |
| 2007/0009459 A1 | 1/2007 | Magnant et al. |
| 2011/0076309 A1* | 3/2011 | Misner et al. ............... 424/401 |

FOREIGN PATENT DOCUMENTS

| | | |
|---|---|---|
| JP | 62-111912 | 5/1987 |
| WO | WO 91/18588 | 12/1991 |
| WO | WO 92/16148 | 10/1992 |
| WO | WO 97/46246 | 12/1997 |
| WO | WO99/11233 | 3/1999 |
| WO | WO 01/39730 | 6/2001 |
| WO | WO01/70185 A2 | 9/2001 |
| WO | WO 03/010273 | 2/2003 |

OTHER PUBLICATIONS

Search Report for PCT/US2008/051853 (Dated Sep. 22, 2008).
Search Report for PCT/US2008/051803 (Dated Sep. 22, 2008).

* cited by examiner

ANTIPERSPIRANT/DEODORANT COMPOSITIONS

CROSS REFERENCE TO RELATED APPLICATIONS

This application is a continuation in part of U.S. application Ser. No. 11/670,481 filed on 2 Feb. 2007 which is incorporated herein by reference.

BACKGROUND OF THE INVENTION

The majority of anhydrous antiperspirant/deodorant compositions contain a stearyl alcohol or n-alkane as a primary gellant and to provide a stable composition matrix. Alternative gellant options, most notably triglycerides from plant and animal tissues, have been explored and found to result in significant formulation changes, at increased cost. Use of these triglycerides in the composition often does not provide a desirable application or cosmetic aesthetic, providing a less structurally stable composition that leaves a visible residue.

It would be desirable to include a hydrogenated soybean oil into an antiperspirant/deodorant composition to provide a similar or improved structure over existing compositions or improve the aesthetics of the composition.

SUMMARY OF THE INVENTION

A composition comprising:
i) at least one active chosen from at least one antiperspirant active and at least one deodorant active;
ii) a first gellant chosen from at least one fatty alcohol and at least one hydrocarbon of the formula $C_nH_{2n+2}$, wherein n is about 20 to about 100, and the hydrocarbon is at least 90% linear;
iii) at least one soybean oil having an iodine value of greater than 0 to about 20; and
iv) at least one silicone.

A method is provided for increasing the compression force of a composition comprising adding at least one soybean oil having an iodine value of greater than 0 to about 20 to the composition, wherein the composition comprises:
i) at least one active chosen from at least one antiperspirant active and at least one deodorant active;
ii) at least one hydrocarbon of the formula $C_nH_{2n+2}$, wherein n is about 20 to about 100, and the hydrocarbon is at least 90% linear; and
iii) at least one silicone.

A method is provided for increasing the fragrance retention of a composition comprising adding at least one soybean oil having an iodine value of greater than 0 to about 20 to the composition, wherein the composition comprises:
i) at least one active chosen from at least one antiperspirant active and at least one deodorant active;
ii) at least one fatty alcohol; and
iii) at least one silicone.

DETAILED DESCRIPTION OF THE INVENTION

Figure 1:
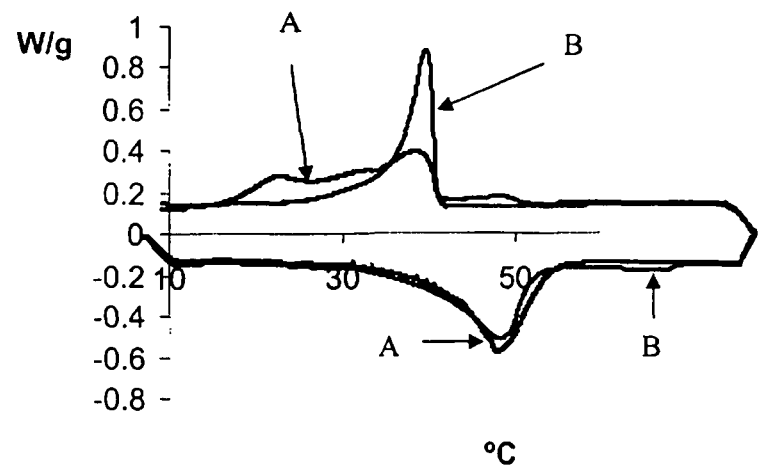
FIG. 1 is a Differential Scanning Calorimetry (DSC) graph of a composition containing stearyl alcohol as a gellant along with hydrogenated soybean oil as a co-gellant as compared to a composition containing stearyl alcohol as a gellant along with hydrogenated castor oil as a co-gellant.

As used throughout, ranges are used as a shorthand for describing each and every value that is within the range. Any value within the range can be selected as the terminus of the range.

The composition is a solid stick or soft solid when at ambient room temperature of about 25° C. The stick form is an example of a solid form, and the soft solid is a thickened form that may or may not be solid. The stick form can be distinguished from a soft solid in that, in a stick, the formulated product can retain its shape for extended time periods outside the package, the product not loosing its shape significantly (allowing for some shrinkage due to solvent evaporation). Adjustment of amounts of gelling or thickening agents can be used in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons", and hereinafter are generically called "soft solids". Reference is made to U.S. Pat. No. 5,102,656, U.S. Pat. No. 5,069,897, and U.S. Pat. No. 4,937,069, each of which discloses such soft solids, including physical characteristics thereof such as viscosity and hardness. The contents of each of these three U.S. Patents are incorporated herein by reference to the extent that they do not conflict with the disclosure herein.

Gelling Agents

Gelling agents used in the present invention comprise hydrogenated soybean oil and a first gellant comprising a fatty alcohol and/or a hydrocarbon of the formula $C_nH_{2n+2}$, wherein n is about 20 to about 100, and the hydrocarbon is at least 90% linear.

The hydrogenated soybean oil is used as a co-gellant along with the first gellant to provide a solid stick or soft solid antiperspirant. The hydrogenated soybean oil is almost, but not fully hydrogenated. The amount of hydrogenation is measured by the iodine value. The iodine value can be measured by ASTM D5554-95 (2006). The iodine value of the hydrogenated soybean oil used herein is greater than 0 to about 20. In one embodiment, the iodine value is 1 to 5. It has been found that this level of hydrogenation provides the desired structure to the antiperspirant and provides a softer and creamier application aesthetics.

The hydrogenated soybean oil is present in an amount up to about 20% by weight of the composition. In another embodiment, the amount is up to about 10% by weight. In one embodiment, the amount is about 3 to about 7% by weight. In another embodiment, the amount is about 4 to about 6% by weight.

The hydrogenated soybean oil can provide increased fragrance longevity when used to replace hydrogenated castor oil.

The fatty alcohol can be any fatty alcohol. In one embodiment, the fatty alcohol is stearyl alcohol.

The hydrocarbon is a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene. An example of a polyethylene can be found in U.S.

Pat. No. 6,503,491, which is incorporated herein by reference only for its disclosure of the polyethylene. In another embodiment, the polyethylene has a weight average molecular weight in of about 300 to about 3000 and a melting point of about 50 to about 129° C.

In one embodiment, the first gellant is present in the composition in an amount of about 5 to about 25% by weight of the composition. In another embodiment, the amount is about 10 to about 20% by weight.

The formulations of the invention may further comprise additional gelling agents, which include, but are not limited to, waxes, esters of fatty acid and fatty alcohol, triglycerides, or other cosmetically acceptable materials, which are solid or semi solid at room temperature and provide a consistency suitable for application to the skin.

When the hydrogenated soybean oil is used in combination with the fatty alcohol, the resulting structure crystallizes at lower temperature. The following samples were prepared to show this effect.

|  | A | B (control) |
|---|---|---|
| Cyclomethicone | 35.6 | 35.6 |
| Stearyl alcohol | 17 | 17 |
| C12-15 alkyl benzoate | 10 | 10 |
| PPG14 butyl ether | 5 | 5 |
| CASTORWAX ™ MP80 | 2.8 | 7.4 |
| Hydrogenated soybean oil | 4.6 | 0 |
| PEG-8 distearate | 3 | 3 |
| Talc | 2 | 2 |
| Antiperspirant AZP908 | 20 | 20 |

DSC (Differential Scanning Calorimetry) was measured using a TA instrument 2920 MDSC. Both samples showed one crystallization peak having a peak temperature of 39.5° C. For the hydrogenated soybean oil sample, the area under this peak was reduced in half and two additional broad peaks were observed at lower temperatures. Unlike the CASTORWAX™ MP80 only containing sample, no peak corresponding to the crystallization of hydrogenated soybean oil was observed. It is theorized that the hydrogenated soybean oil experiences "super-cooling" and can co-crystallize with stearyl alcohol, which is shown by the additional peaks at lower temperature in FIG. 1. The DSC graph is shown in FIG. 1 as heat flow (W/g) vs. Temperature (° C.). The curves shown correspond to the compositions shown above.

The difference in composition structure can also be seen in the compression values. In Example 3 below, the compression values change as the amount of hydrogenated soybean oil changes.

When using the hydrogenated soybean oil as a co-gellant with the fatty alcohol gellant, the composition has increased fragrance retention as compared to compositions containing hydrogenated castor oil. This effect is shown below in Example 4. After aging, the compositions containing hydrogenated soybean oil had more fragrance remaining in the composition as measured using head space analysis. In one embodiment, the composition has an average fragrance intensity of at least $5 \times 10^5$ μVs as measured using the procedure in Example 4. In another embodiment, the average fragrance intensity is at least about $5.1 \times 10^5$ μVs, at least about $5.2 \times 10^5$ μVs, at least about $5.5 \times 10^5$ μVs, or at least about $5.8 \times 10^5$ μVs.

When the hydrogenated soybean oil is used in combination with the hydrocarbon based gellant, the structure, as measured by compression force, is increased as compared to a composition that contains hydrogenated castor oil. When hydrogenated soybean oil replaces hydrogenated castor oil (CASTORWAX™ MP80) in an equal amount by weight in a composition with all other materials remaining the same (see Example 5 below), the ratio of the compression force of the composition with the hydrogenated soybean oil to the compression force of the composition with the hydrogenated castor oil is greater than 1.3. In other embodiments, the ratio is greater than 1.4, 1.5, or 1.6.

In one embodiment, the compression force of the composition is at least about 3500 g. In other embodiments, the compression force is at least about 4000 g, at least about 4500 g, at least about 5000 g, at least about 6000 g, at least about 7000 g, at least about 8000 g, at least about 9000 g. In another embodiment, the compression force is about 3500 g to about 10,000 g.

Figure 2:
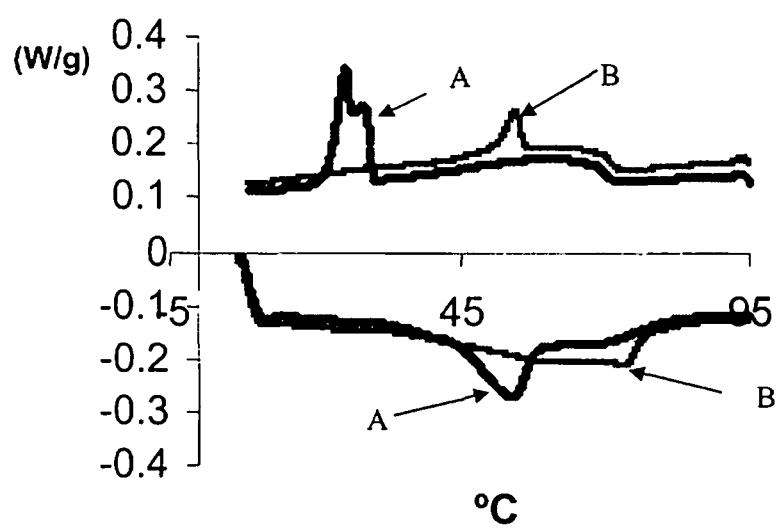
FIG. 2 is a Differential Scanning Calorimetry (DSC) graph of a composition containing polyethylene as a gellant along with hydrogenated soybean oil as a co-gellant as compared to a composition containing polyethylene as a gellant along with hydrogenated castor oil as a co-gellant.

DSC (Differential Scanning Calorimetry) was measured using a TA instrument 2920 MDSC. In the sample using hydrogenated soybean oil, the crystallization is deferred to a lower temperature. The melting and crystallization peaks are stronger with hydrogenated soy, which indicates a more crystalline composition. The DSC graph is shown in FIG. 2 as heat flow (W/g) vs. Temperature (° C.). The curves shown correspond to the compositions shown below.

|  | Sample A | Sample B |
|---|---|---|
| Polyethylene 400 | 10 | 10 |
| H-soybean oil | 6.5 | 0 |
| CASTORWAX ™ MP80 | 0 | 6.5 |
| Cyclomethicone | 42.5 | 42.5 |
| C12-15 alkyl benzoate | 15 | 15 |
| Al Zr Tetrachlorohydrex Gly | 22 | 22 |
| PEG-8 distearate | 4 | 4 |

In one embodiment, the composition can provide a payout of about 0.7 to about 0.9 g according to the payout test on the Payout, Glide, and Flakeoff Test Machine. In another embodiment, the composition can provide a glide of about 0.8 to about 1.4 g according to the glide test on the Payout, Glide, and Flakeoff Test Machine. In anther embodiment, the composition can provide a flakeoff of less that about 25%. In other embodiments, the flake off is less than about 20, about 15, about 10, or about 5%. In other embodiments, the amount of flakeoff is about 1 to about 6%.

As used in this specification, Payout, Glide, and Flakeoff Test Machine refers to the system described in U.S. application Ser. No. 11/971,978, filed on 10 Jan. 2008, 61/015, 852, filed on 21 Dec. 2007, and 60/976,527 filed on 1 Oct. 2007, all of which are incorporated herein by reference. The text from Serial No. is reproduced in the Appendix below. See the following sections in the Appendix for the parameters for measuring payout ([Appendix 0039] and [Appendix 0055]), glide ([Appendix 0039] and [Appendix 0060]), and flakeoff ([Appendix 0036]).

Volatile Silicone

Compositions according to the present invention include a volatile silicone. In one embodiment, the volatile silicone is a volatile cyclic polydimethylsiloxane (cyclomethicone), e.g., cyclopentasiloxane. By volatile material it is meant that the material has a measurable vapor pressure at ambient temperature. Preferably, the volatile cyclic polydimethylsiloxane is cyclomethicone. Various types of cyclomethicones may be used. Illustratively, and not by way of limitation, the volatile silicones are one or more members selected from cyclic polydimethylsiloxanes such as those represented by Formula I:

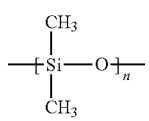

where n is an integer with a value of 3-7, particularly 5-6. Illustrative examples of suitable cyclomethicones are DC-345 and DC-245, manufactured by Dow Corning Corporation, Midland, Mich. These types include a tetramer (octylmethylcyclotetrasiloxane) and a pentamer (decamethylcyclopentasiloxane). In one embodiment, the amount of volatile silicone in the composition is about 5 to about 70% by weight of the composition. In another embodiment, the amount is about 25 to about 45% by weight.

Antiperspirant Active Materials

When the composition includes an antiperspirant active, any of the known antiperspirant active materials can be utilized in the composition. Antiperspirant actives include, but are not limited to, aluminum chlorhydrate, aluminum chloride, aluminum sesquichlorohydrate, aluminum-zirconium hydroxychliorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the Betaine:Zr mole ratio is about 0.2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZALTυ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorhydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Deodorant Active Materials

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats.

Emollients

The composition can contain emollients in any desired amount to achieve a desired emollient effect. Emollients are known in the art and are used to impart a soothing effect on the skin. Non-volatile emollients are preferable in the present invention. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material in the present invention is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can additionally include ionizable inorganic salts. These ionizable salts are of the form $M_aX_b$ where a=1, or 2 and b=1 or 2; M is a member chosen from $Na^{+1}$, $Li^{+1}$, $K^{+1}$, $Mg^{+2}$, $Ca^{+2}$, $Sr^{+2}$, and $Zn^{+2}$ and X is a member chosen chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In certain embodiments, the selected salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water. Of course various concentrations of the salt premix can be made.

The composition may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is sized so that it can pass through the application to prevent the ball applicator from malfunctioning. Usually, the average particle size does not exceed 150 microns.

In certain embodiments, the composition may also contain as an optional ingredient at least one malodor counteracting alpha, beta-unsaturated ester or mixtures of such materials. In certain embodiments, the level of malodor counteracting composition to deliver a perceivable odor control benefit when delivered from an antiperspirant and/or deodorant composition is about 0.05 to about 0.45 weight % based on the entire composition. The alpha, beta-unsaturated ester malodor counteracting materials are incorporated within the oil phase of an antiperspirant composition. Example of these malodor counteracting components can be found in U.S. Pat. No. 6,610,648 and U.S. Pat. No. 6,495, 097, which are incorporated herein only for their disclosure of the alpha, beta unsaturated esters. For example, in this invention the odor neutralizing alpha, beta unsaturated ester mixture demonstrates unexpected stability in antiperspirant compositions containing low metal:chloride (M:Cl) ratio salts free of glycine. Examples of the alpha, beta unsaturated ester can be found in WO2005/025523, which was filed in the United States as U.S. application Ser. No. 10/571,488, both of which are incorporated herein by reference to the extent that they do not conflict with the disclosure in this specification.

Examples of the alpha, beta unsaturated ester include, but are not limited to:

(1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl; and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group; and (2) an ester of fumaric or maleic acid having linear ester carbon chains from 3-9 carbons, for example dihexyl fumarate;

(3) e-phenyl propenoic acid ester chosen from octyl methoxy cinnamate, phenylethyl cinnamate, benzyl cinnamate;

(4) an aliphatic unsaturated ester, such as diliexyl fumarate.

The composition may optionally further comprise absorbent materials such as corn starch, talc, clay, sodium polyacrylate and/or cotton fiber; and/or other materials such as fragrances, bacteriostats and/or bacteriosides, colorants, etc. Known bacteriostats include baceteriostatic quaternary ammonium compounds such as 2-amino-2-methyl-1-propanol (AMP), cetyl-trimethylammomium bromide, cetyl pyridinium chloride, 2,4,4N-trichloro-2N-hydroxydiphenylether (Triclosan), etc. and various zinc salts.

Antioxidants may be added to the composition, preferably to act as ingredient protectants and for maintenance of long-term stability of the composition. Suitable antioxidants include Tinogard, manufactured by Ciba Specialty Chemicals, Basel, Switzerland.

The compositions as provided herein are described and claimed with reference to their ingredients, as is usual in the art. As would be evident to one skilled in the art, ingredients may in some instances react with one another, so that the true composition of the final formulation may not correspond exactly to the ingredients listed. Thus, it should be understood that the invention extends to the product of the combination of the listed ingredients.

The compositions of the present invention may be manufactured using methods known in the art. Typically, the ingredients are combined and heated to melt the components (other than inert filler), and the melted components (together with particulate inert filler) are mixed. Desirably, volatile materials, such as the fragrance materials, are incorporated in the composition in the latter stages of the mixing cycle, in order to avoid volatilization thereof. After mixing, the molten composition can be poured directly into the dispensers, after which the compositions harden into a solid, and the container is capped to preserve the product until use.

In the following are set forth examples of the present invention. These examples are illustrative, and not limiting, of the present invention. In the following examples, all amounts are in percent of the total weight of the composition.

The hydrogenated castor oil in the examples is CASTORWAX™ from CasChem, Inc. The product number after the name indicates the melting point of the hydrogenated castor oil. The iodine value of the hydrogenated soybean oil used in the examples is greater than 0 to 1. The weight average molecular weight of the polyethylene used in the examples is indicated by the product number.

To make the compositions, emollients are placed in a 600 ml beaker. The emollients are heated with stirring to 65° C. The gellants are added, and the mixture is heated to 82-85° C. The mixture is cooled to about 80° C., and cyclomethicone, which is preheated to about 70° C., is added. The mixture is cooled to about 75° C. and the antiperspirant is added. The temperature is increased to about 80° C. and held for about 10 minutes, and the remaining ingredients are added and mixed for one minute. The mixture is poured into oval containers of the type used for antiperspirants/deodorants, and they are placed in a refrigerator at 4° C. for 15 minutes. Cooling is completed at room temperature.

Compression is measured using a Texture Analyzer (model #TA-XT21 from Texture Technologies Corp) fitted with a 19 mm square end probe. The antiperspirant stick is removed from the barrel and placed in a hardness sample holder. The sample is positioned so that 2.54 cm (1 inch) of the sample, measured at edge of domed portion is exposed from the Compression Holder for the test. The cover on the hardness holder is closed, and the holder is positioned so that the blade will come in contact at the midpoint of the exposed sample. The instrument is set to run at 1.0 mm/s at a distance of 5.0 mm. The peak value of the compression curve is recorded as the stick hardness value in grams.

EXAMPLE 1

| Stick Composition | Control | With Hydrogenated Soybean Oil |
|---|---|---|
| Cyclomethicone DC245 | 34.76 | 34.76 |
| C$_{12-15}$ alkyl benzoate | 10.19 | 10.19 |
| Stearyl alcohol | 19.22 | 19.22 |
| CASTORWAX ™ MP80 | 6.12 | 0 |
| PEG-8 distearate | 3.06 | 3.06 |
| Hydrogenated soybean oil | 0 | 6.12 |
| Antiperspirant Z576 | 20.38 | 20.38 |
| PPG-14 butyl ether | 4.08 | 4.08 |
| Talc | 2.04 | 2.04 |
| Behenyl alcohol | 0.15 | 0.15 |
| Compression (grams force) | 3629 | 3729 |

Example 1 shows that in a stick composition made with replacing CASTORWAX™ with hydrogenated soybean oil in an equal amount resulted in a stick with a comparable compression force (structure).

EXAMPLE 2

| | Control | With hydrogenated soybean oil |
|---|---|---|
| Phenyl trimethicone | 5 | 5 |
| Cyclomethicone | 36.9 | 36.9 |
| Stearyl alcohol | 18 | 18 |
| Hydrogenated castor oil MP70 | 2 | 0 |
| Hydrogenated castor oil MP90 | 2 | 0 |
| PEG-8 distearate | 2 | 2 |
| PPG-14 butyl ether | 12.1 | 12.1 |
| Antiperspirant AZP908 | 22 | 22 |
| Hydrogenated soybean oil | 0 | 4 |
| Compression (grams force) | 2550 | 1350 |
| Product form | stick | soft solid |

Example 2 shows that it is possible to change the product form by using hydrogenated soybean oil depending on the formulation.

EXAMPLE 3

The compression force was measured for several compositions containing stearyl alcohol as the gellant with varying amounts of hydrogenated castor oil and hydrogenated soybean oil. The compositions are shown in the table below along with the compression measurements. The results show that the using hydrogenated soybean oil in combination with a fatty alcohol gelling agent, the structure of the composition is changed as indicated by the compression values.

| | 3A | 3B | 3C | 3D |
|---|---|---|---|---|
| PPG-14 butyl ether | 6 | 6 | 6 | 6 |
| C12-15 alkyl benzoate | 10 | 10 | 10 | 10 |
| Hydrogenated soybean oil | 0 | 2 | 5 | 7 |
| CASTORWAX ™ MP80 | 7 | 5 | 2 | 0 |
| PEG-8 distearate | 3 | 3 | 3 | 3 |
| Stearyl alcohol | 16 | 16 | 16 | 16 |
| Behenyl alcohol | 0.15 | 0.15 | 0.15 | 0.15 |
| Cyclomethicone | 33.95 | 33.95 | 33.95 | 33.95 |
| Talc | 2 | 2 | 2 | 2 |
| Al Zr Tetrahydrachlorex Gly | 20 | 20 | 20 | 20 |
| Fragrance | 1 | 1 | 1 | 1 |
| Encapsulated Fragrance | 0.9 | 0.9 | 0.9 | 0.9 |
| Compression (g) | 3354.07 | 3262.29 | 2121.8 | 363.5 |
| Standard Deviation | 35.44 | 83.38 | 303.85 | 60.45 |

EXAMPLE 4

The formula in the table below is used for Example 4. Samples are prepared with no hydrogenated castor oil and no hydrogenated soybean oil, 4% or 8% weight hydrogenated castor oil (CASTORWAX™ MP80), and 4% or 8% by weight hydrogenated soybean oil.

| | Weight % |
|---|---|
| Cyclomethicone | 35.6 |
| C12-15 alkyl benzoate | 10 |
| PPG14 butyl ether | 5 |
| PEG-8 distearate | 3 |
| Talc | 2 |
| Antiperspirant AZP908 | 20 |
| CASTORWAX ™ MP80 | 0, 4, or 8 |
| Hydrogenated soybean oil | 0, 4, or 8 |
| Stearyl alcohol | Balance |

A layer of AP stick under study (0.3 gram) is applied evenly on the surface of a 2.54 cm×5.08 cm (1"×2") wool flannel (style 527 from Testfabrics Inc., West Pittston, Pa.). The samples are then placed into a 37° C. oven. After 5 hours, the samples are taken out of the oven and sealed into glass vials for Headspace Gas Chromatography analysis (Perkin Elmer HS 40×1 headspace sampler coupled with Varian Star 3400 CX Gas Chromatograph). Each formula has 3 replicates. The average for each is reported in the table below.

| Formulas | Averaged fragrance intensity (5 hour aging), ×$10^5$ μVs |
|---|---|
| No co-gellant | 5.8 |
| 4% CASTORWAX ™ MP80 | 4.9 |
| 8% CASTORWAX ™ MP80 | 4.1 |
| 4% hydrogenated soybean oil | 5.8 |
| 8% hydrogenated soybean oil | 5.2 |

The results above show that formulations using hydrogenated soy as a co-gellant retain more fragrance in the composition after aging as compared to formulations containing castor wax.

EXAMPLE 5

|  | 5A | 5B | 5C | 5D | 5E | 5F |
|---|---|---|---|---|---|---|
| Cyclomethicone DC345 | 42 | 42 | 42 | 42 | 42 | 42 |
| Polyethylene PE400 | 5 | 5 | 12 | 12 | 0 | 0 |
| Polyethylene PE500 | 5 | 5 | 0 | 0 | 12 | 12 |
| Polyethylene PE655 | 2 | 2 | 0 | 0 | 0 | 0 |
| H-soybean oil | 0 | 5 | 0 | 5 | 0 | 5 |
| CASTORWAX ™ MP80 | 5 | 0 | 5 | 0 | 5 | 0 |
| C12-15 alkyl benzoate | 15 | 15 | 15 | 15 | 15 | 15 |
| Antiperspirant AZP910 Gold | 22 | 22 | 22 | 22 | 22 | 22 |
| PEG-8 distearate | 4 | 4 | 4 | 4 | 4 | 4 |
| Compression (g force) | 2912 | 4841 | 3205 | 5112 | 3072 | 4550 |

In Example 5, it can be seen that the replacement of CASTORWAX™ (hydrogenated castor oil) with the hydrogenated soybean oil in equal amounts resulted in increased structure as measured by the compression force.

Examples 6-8 below show further compositions according to the invention.

EXAMPLE 6

|  | Wt. % |
|---|---|
| Aluminum-zirconium tetrachlorohydrex gly | 20-21 |
| Stearyl alcohol | 19-20 |
| Cyclomethicone | 34-35 |
| PPG-14 butyl ether | 4-6 |
| PEG-8 distearate | 1-3 |
| $C_{12-15}$ Alkyl benzoate | 8-10 |
| Hydrogenated soybean oil | 5-7 |
| Talc | 2-4 |
| Behenyl alcohol | 0.1-0.3 |

EXAMPLE 7

|  | Wt. % |
|---|---|
| Aluminum-zirconium tetrachlorohydrex gly | 20-21 |
| Stearyl alcohol | 15-16 |
| Hydrogenated castor oil | 3-5 |
| Cyclomethicone | 36-38 |
| Myristyl Myristate | 1-3 |
| PEG-8 distearate | 1-3 |
| $C_{12-15}$ Alkyl benzoate | 7-9 |
| Hydrogenated soybean oil | 1-3 |
| PPG-3 myristyl ether | 5-7 |
| Talc | 2-4 |
| Behenyl alcohol | 0.1-0.3 |

EXAMPLE 8

|  | Wt. % |
|---|---|
| Aluminum-zirconium tetrachlorohydrex gly | 20-21 |
| Stearyl alcohol | 20-21 |
| Hydrogenated castor oil | 4-6 |
| Cyclomethicone | 33-35 |
| PEG-8 distearate | 1-3 |
| Phenyl trimethicone | 1-3 |
| $C_{12-15}$ Alkyl benzoate | 4-6 |
| Hydrogenated soybean oil | 7-9 |
| Talc | 2-4 |
| Behenyl alcohol | 0.1-0.3 |

What is claimed is:

1. A composition comprising:
   i) at least one active chosen from at least one antiperspirant active and at least one deodorant active;
   ii) from about 5% to about 25% by weight of the composition of a first gellant, the first gellant chosen from at least one fatty alcohol and at least one hydrocarbon of the formula $C_nH_{2n+2}$, wherein n is about 20 to about 100, and the hydrocarbon is at least 90% linear;
   iii) an amount of about 3% to about 10% by weight of a co-gellant, the co-gellant comprising hydrogenated soybean oil having an iodine value of greater than 0 to about 20;
   iv) an amount of about 5% to about 25% of at least one volatile silicone; and
   v) an amount of about 12% to about 16% by weight of a combination of emollients consisting of PPG-3 myristyl ether and $C_{12-15}$ alkyl benzoate.

2. The composition of claim 1, wherein the soybean oil is present in an amount of about 3 to about 7% by weight of the composition.

3. The composition of claim 1, wherein the first gellant comprises the fatty alcohol.

4. The composition of claim 3, wherein the fatty alcohol comprises stearyl alcohol.

5. The composition of claim 1, wherein the first gellant comprises the hydrocarbon.

6. The composition of claim 5, wherein the hydrocarbon comprises polyethylene.

7. The composition of claim 1, wherein the volatile silicone comprises cyclomethicone.

8. The composition of claim 1, wherein the antiperspirant active is present in an amount of about 10 to about 25% by weight of the composition.

9. The composition of claim 1, wherein the deodorant active is present in an amount of greater than 0 to about 1% by weight of the composition.

10. The composition of claim 1, wherein the composition is a solid stick or soft solid.

11. The composition of claim 1, wherein the composition has a payout of about 0.7 to about 0.9 g according to a payout test on a Payout, Glide, and Flakeoff Test machine.

12. The composition of claim 1, wherein the composition has a glide of about 0.8 to about 1.4 g according to a glide test on a Payout, Glide, and Flakeoff Test machine.

13. The composition of claim 1, wherein the composition has a flakeoff of less than about 25%.

14. The composition of claim 1 further comprising at least one malodor counteracting alpha, beta-unsaturated ester.

15. The composition of claim 1, wherein the volatile silicone comprises cyclomethicone.

16. The composition of claim 1, wherein the iodine value is about 20.

17. The composition of claim 1, comprising no hydrogenated oil.

18. A method comprising applying the composition of claim 1 to an axillary area.

* * * * *